(12) United States Patent
Zhao

(10) Patent No.: US 6,204,381 B1
(45) Date of Patent: Mar. 20, 2001

(54) PROCESS FOR THE PREPARATION OF TRIAZINE CARBAMATES

(75) Inventor: Hong Zhao, Millbury, MA (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/313,777

(22) Filed: May 17, 1999

Related U.S. Application Data

(60) Provisional application No. 60/089,453, filed on Jun. 16, 1998.

(51) Int. Cl.$^7$ ....................... C07D 251/50; C07D 251/70
(52) U.S. Cl. ......................... 544/189; 544/196; 544/197; 544/204; 544/208
(58) Field of Search ................................... 544/189, 196, 544/197, 204, 208

(56) References Cited

U.S. PATENT DOCUMENTS

| | | | |
|---|---|---|---|
| 4,444,954 | 4/1984 | Mels et al. | 525/124 |
| 4,939,213 | 7/1990 | Jacobs, III et al. | 525/329.9 |
| 5,084,541 | 1/1992 | Jacobs, III et al. | 528/45 |
| 5,233,003 | 8/1993 | Lucas et al. | 526/301 |
| 5,288,865 | 2/1994 | Gupta | 544/200 |
| 5,556,971 | 9/1996 | Bay et al. | 544/196 |
| 5,672,703 | 9/1997 | Ramesh et al. | 544/194 |
| 5,852,133 | 12/1998 | Gupta et al. | 525/375 |

FOREIGN PATENT DOCUMENTS

| | | |
|---|---|---|
| 0 604 922 A1 | 12/1993 | (EP) . |
| 0 624 577 A1 | 5/1994 | (EP) . |
| WO 93/10117 | 5/1993 | (WO) . |
| WO 96/04258 | 2/1996 | (WO) . |
| WO 96/11915 | 4/1996 | (WO) . |

*Primary Examiner*—Richard L. Raymond
*Assistant Examiner*—Venkataranau Balasubramanian
(74) *Attorney, Agent, or Firm*—Claire M. Schultz; Valerie T. Didamo; Liza Negron

(57) ABSTRACT

Disclosed is the preparation of 1,3,5-triazine carbamates which are suitable for use as crosslinking agents in curable compositions, particularly in coating compositions which are capable of curing at relatively low temperatures without releasing formaldehyde during cure. The process includes the step of contacting a 1,3,5-triazine derivative having cyanate-displaceable leaving groups (i.e. cyanuric chloride), a cyanate-containing reagent (i.e. potassium cyanate), and an isocyanate-reactive compound such as an alcohol, in the presence of a polar solvent or in the presence of a non-polar solvent in combination with a phase transfer catalyst.

33 Claims, No Drawings

PROCESS FOR THE PREPARATION OF TRIAZINE CARBAMATES

This application claims priority under 35 U.S.C. §119 from U.S. Provisional Application Ser. No. 60/089,453 (filed Jun. 16, 1998), which is incorporated by reference herein as if fully set forth.

BACKGROUND OF THE INVENTION

1. Field of the Invention

This invention relates to the preparation of 1,3,5-triazine carbamates which are suitable for use as crosslinking agents in curable compositions, particularly in coating compositions capable of curing at relatively low temperatures without releasing formaldehyde during cure.

2. Description of the Related Art

Various derivatives of amino-1,3,5-triazines are described in the literature as being utilized in a wide variety of fields. An important use of certain of these derivatives, such as the methoxymethyl derivatives of melamine and guanamine, is as crosslinkers and/or reactive modifiers in curable compositions which contain resins having active hydrogen groups. While these methoxymethyl derivatives provide excellent results in a number of aspects, they also have the disadvantage of releasing formaldehyde as a volatile by-product under curing conditions. It has long been a desire of industry to find acceptable alternatives which do not emit formaldehyde during cure.

One such non-formaldehyde alternative that has shown great promise is the class of isocyanate and carbamate-functional 1,3,5-triazine crosslinking agents disclosed in commonly owned U.S. Pat. Nos. 4,939,213, 5,084,541 and 5,288,865, EP-A-0604922 (corresponding to U.S. application Ser. No. 07/998,313, filed Dec. 29, 1992), EP-A-0624577 (corresponding to U.S. application Ser. No. 08/061,905, filed May 14, 1993), U.S. application Ser. No. 08/138,581 (filed Oct. 15, 1993), U.S. application Ser. No. 08/239,009 (filed May 6, 1994), U.S. application Ser. No. 08/286,835 (filed Aug. 5, 1994), U.S. application Ser. No. 08/324,549 (filed Oct. 18, 1994) and U.S. application Ser. No. 08/08/705,472 (filed Aug. 29, 1996), which are incorporated by reference herein for all purposes as if fully set forth. Specifically, the carbamate functional 1,3,5-triazines disclosed in these references have been found to be particularly useful as crosslinkers in coating compositions based upon hydroxy functional resins, with the cured coatings possessing a wide range of desirable properties.

Other non-formaldehyde emitting alternatives include, for example, the class of lactam substituted 1,3,5-triazine crosslinking agents disclosed in commonly owned WO 93/10117 (corresponding to U.S. application Ser. No. 07/973,676, filed Nov. 9, 1992) and the class of acetal and enamine functional 1,3,5-triazine crosslinking agents disclosed in commonly owned U.S. application Ser. No. 08/408,323 (filed Mar. 21, 1995), which are also incorporated by reference herein for all purposes as if fully set forth.

While some of these these non-formaldehyde emitting systems have shown great promise, their preparation methods can be somewhat cumbersome, difficult and expensive. For example, in previously incorporated U.S. Pat. No. 4,939,213 and U.S. Pat. No. 5,084,541, the 1,3,5-triazine carbamates are produced in a two-step process by first reacting an amino-1,3,5-triazine with oxalyl chloride to produce an isocyanate functional intermediate, then reacting this intermediate with an alcohol. Further, in previously incorporated U.S. Pat. No. 5,288,865, carbamate functional 1,3,5-triazines are produced in a one-step process by reacting a haloamino-1,3,5-triazine with an acid halide. The primary disadvantage of these processes include the use of certain costly halogenated starting materials, production of substantial amounts of halogenated by-products, and low ultimate yield of the desired products. Therefore, the search continues for simple and economical routes to preparing non-formaldehyde crosslinkers.

Some of the problems with these processes have been solved by the process disclosed in previously incorporated U.S. application Ser. No. 08/061,905, wherein carbamate functional 1,3,5-triazines are produced by reacting an at least bis-amino 1,3,5-triazine with an acyclic organic carbonate in the presence of a strong base. Disadvantages to this process include, for example, that the strong base must be neutralized to remove it from the end product and that certain aspects of the reaction must be carefully controlled in order to avoid color in the end product.

In regard to the production of mono-carbamates, Matsui and Otaguro, 1976, Kogyo Kagaku Zasshi, 67: 12, pp. 2402–2403 describe the formation of a mono-substituted product, 2-(ethoxycarbonylamino)-4,6-dichloro-1,3,5-triazine, from the reaction of cyanuric chloride with potassium cyanate. However, the attainment of di-substituted derivatives are not therein disclosed.

It has now been surprisingly discovered that di- and more highly substituted 1,3,5-triazine carbamate crosslinkers can be produced by reacting, in an organic solvent reaction medium, (i) a 1,3,5-triazine derivative having thereon at least two cyanate displacable leaving groups and (ii) a cyanate-containing reagent, in the presence of (iii) an isocyanate-reactive compound, such as a hydroxy-functional compound. The process of the present invention advantageously does not require any costly starting materials. Furthermore, the 1,3,5-triazine carbamate crosslinkers prepared by the present invention's process can be produced directly, without handling of the 1,3,5-triazine intermediates. When employed in coating compositions, the 1,3,5-triazine carbamate crosslinkers produced by the present invention's process produce films which have good appearance, solvent resistance and gloss characteristics.

SUMMARY OF THE INVENTION

In accordance with the present invention, there is provided a process for preparing a 1,3,5-triazine carbamate derivative having the formula (I) or an oligomer thereof:

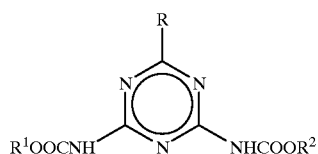

wherein R is selected from the group consisting of —NHCOOR$^3$, hydrogen, hydrocarbyl, hydrocarbyloxy, hydrocarbylthio, amido, sulfonamido, amino and a leaving group; and wherein R$^1$, R$^2$ or R$^3$ is, independently, a hydrocarbyl or a hydrocarbyloxyhydrocarbyl, said process comprising the step of contacting:

(i) a 1,3,5-triazine derivative having at least two cyanate-displaceable leaving groups represented by the formula (II) or an oligomer thereof:

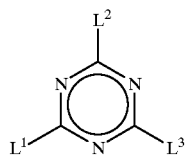

wherein $L^1$ is selected from the group consisting of hydrogen, hydrocarbyl, hydrocarbyloxy, hydrocarbylthio, amido, sulfonamido, amino and a leaving group; and wherein each of $L^2$ and $L^3$ is, independently, a leaving group;

(ii) a cyanate-group containing reagent capable of reaction therewith;

(iii) an isocyanate-reactive compound; and (iv) an isocyanate-unreactive organic solvent, wherein said contacting is carried out at a temperature and length of time sufficient to produce a 1,3,5-triazine carbamate derivative having at least two carbamate groups, with the proviso that if the organic solvent is not sufficiently polar to produce a bis-carbamate derivative, contacting is carried out in the presence of a phase-transfer catalyst.

An important use of the 1,3,5-triazine carbamates produced by the novel process of the present invention is based on their ability to act as crosslinking agents in curable compositions, and especially those curable compositions which contain polyfunctional materials which have active hydrogen groups. The 1,3,5-triazine carbamates of the present invention therefore find use, for example, in coatings, adhesives and molding applications.

As indicated above, the advantages of the present process include, for example:

(1) the present process does not require the use of environmentally undesirable formaldehyde;

(2) the present process does not require the use of costly halogentated reagents such as oxalyl chloride; and (3) the present process does not require the handling or isolation of an isocyanate intermediate.

These and other features and advantages of the present invention will be more readily understood by those of ordinary skill in the art from a reading of the following detailed description.

DETAILED DESCRIPTION OF THE PREFERRED EMBODIMENTS

As mentioned above, the present invention is a novel process for preparing 1,3,5-triazine carbamate derivatives having at least two carbamate groups.

The term "hydrocarbyl" broadly refers to a group which contains at least carbon and hydrogen atoms and includes, for example, alkyl, aryl, aralkyl, alkenyl, and substituted derivatives thereof.

The term "amido" includes, for example, both substituted and unsubstituted amidos, such as alkyl and/or aryl substituted amido groups.

The term "amino" includes cyclic and non-cyclic amino. For example, the term includes amino, alkyl and/or aryl substituted aminos and heterocyclic N-containing groups optionally containing a different heteroatom in the ring structure. As examples of non-cyclic amino groups may be mentioned an amino group, a monoalkylamino, a monoaralkylamino, a monoarylamino, a dialkylamino, a diaralkylamino and a diarylamino. As examples of cyclic amino groups may be mentioned substituted and unsubstituted pyrrolidino, azepino, piperizino and morpholino groups.

The term "leaving group" means a group which can be displaced by a cyanate compound.

The term "polar organic solvent" in the context of the present invention refers to any solvent having a dipole moment of at least 3.0 Deby Units and includes solvents such as amides, phosphorus-containing compounds, sulfones, sulfoxides, nitrites, carbonates, lactones, nitro compounds, diketones, keto alcohols, and mixtures thereof. Polar organic solvents having a dipole moment of at least 3.0 Deby Units are discussed in detail in U.S. Pat. No. 5,233,003, the contents of which are hereby incorporated by reference herein for all purposes as if fully set forth.

The term "non-polar organic solvent" in the context of the present invention refers to any solvent which has a dipole moment of less than 3.0 Deby Units and includes solvents such as ketones, ethers, esters, hydrocarbons, halocarbons and mixtures thereof.

The 1,3,5-Triazine Starting Material (i)

The 1,3,5-triazine (i) suitable for use in the present invention's process is represented by the formula (II) or an oligomer thereof:

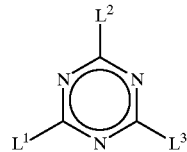

wherein $L^1$ is selected from the group consisting of hydrogen, hydrocarbyl, hydrocarbyloxy, hydrocarbylthio, amido, sulfonamido, amino and a leaving group; and wherein each of $L^2$ and $L^3$ is, independently, a leaving group.

Examples of suitable leaving groups include those which are displaceable by cyanate, for example, halogens, tertiary amines and sulfonates. In a preferred embodiment, groups $L^1$, $L^2$ and $L^3$ of the 1,3,5-triazine starting material are all, independently, a halogen, more preferably groups $L^1$, $L^2$ and $L^3$ are chloride, corresponding to cyanuric chloride.

Cyanate-Group Containing Reagent Capable of Reacting with the 1,3,5-Triazine (ii)

Component (ii) is a cyanate-group containing reagent capable of supplying at least one cyanate group for reaction with the 1,3,5-triazine (i). In a preferred embodiment, the cyanate-group containing reagent is represented by the formula:

$W(NCO)_n$ wherein n is at least 1 and W is an n-functional moiety selected from the group consisting of metal, hydrogen, ammonium, phosphonium, sulfonium, silyl and mixtures thereof.

More preferably, the n-functional moiety, W, is selected from the group consisting of sodium, potassium, quaternary ammonium such as tetraalkylammonium and arylitrialkylammonium, quaternary phosphonium such as methyl triphenylphosphonium and mixtures thereof.

Isocyanate-Reactive Compound (iii)

Component (iii) is an isocyanate-reactive compound capable of reacting with a 1,3,5-triazine isocyanate intermediate to produce a 1,3,5-triazine carbamate. Isocyanate-reactive compounds are well-known in the art and include hydroxy compounds, amines, and mercaptans. Other suitable isocyanate-reactive compounds for use herein include those blocking groups which deblock at relatively low temperatures, e.g., below about 125° C., such as an oxime of an aldehyde or ketone (e.g., methylethyl-ketoxime, acetone oxime and cyclohexanone oxime), N-hydroxyimide (e.g., N-hydroxyphthalimide) and other blocking groups such as those recited in U.S. Pat. No. 4,444,954, the pertinent portions of which are incorporated by reference herein as if fully set forth. Thus, more highly functional oligomeric derivatives of isocyanate functional 1,3,5-triazine intermediates can be produced by including a multifunctional isocyanate-reactive compound.

A wide variety of isocyanate-reactive materials are suitable for use in forming the carbamates and are described in detail in the previously incorporated references. Especially suitable examples of the isocyanate-reactive material useable in forming carbamates are the hydroxy functional compounds, including alcohols, phenols, oximes, hydroxamic ethers, and mixtures thereof. As preferred examples may be mentioned alcohols and phenols, with alcohols being particularly preferred.

As suitable alcohols may be mentioned straight or branched monohydric or polyhydric alkanols and alkenols having 1 to 20 carbon atoms per molecule, monohydric or polyhydric cycloalkanols and cycloalkenols having 3 to 20 carbon atoms in the molecule, and monohydric and polyhydric arylalkyls having 7 to 20 carbon atoms per molecule. Further, these alcohols may also have a substituent such as a halogen atom, a cyano group, an alkoxy group, a sulfone group, a carbonyl group, an ester group, an ether group and an amide group. Mixtures of the above are also suitable.

As preferred alcohols may be mentioned aliphatic linear, cyclic, saturated, or unsaturated alcohols having 1 to 8 carbon atoms, as well as mixtures thereof. As specific preferred examples may be mentioned methanol, ethanol, 1-propanol, 2-propanol, 1-butanol, 2-butanol, iso-butanol, tert-butanol, pentanol, hexanol, cyclohexanol, heptanol, octanol, ethylhexyl alcohol, benzyl alcohol, allyl alcohol, ethylene chlorohydrin, ethylene glycol, propylene glycol, 1,3-propanediol, 1,4-butanediol, ethoxyethanol, hydroxyethoxyethanol, 1-methoxy-2-propanol and mixtures thereof.

As suitable phenols may be mentioned alkyl phenols, alkoxy phenols, halogenated phenols, dihydroxybenzene, 4,4-dihydroxydiphenylmethane, various bisphenols such as bisphenol-A, and hydroxynaphthalenes. Specifically preferred phenols include phenol, 2-methyl phenol, 3-methyl phenol, 4-methyl phenol, 2-chlorophenol, 3-chlorophenol, 4-chlorophenol, catechol, resorcinol, hydroquinone, and mixtures thereof.

A carbamate functional 1,3,5-triazine derivative can readily be produced by adding the isocyanate-reactive compound prior to formation of the isocyanate functional 1,3,5-triazine intermediate or subsequent to the formation of the isocyanate intermediate. A first preferred embodiment of the process of the present invention is to contact components (i), (ii), and (iii) simultaneously in the presence of an organic solvent to produce a 1,3,5-triazine carbamate.

A second preferred embodiment of the novel process is to first contact components (i) and (ii) in the presence of an organic solvent, thereby forming an isocyanate functional 1,3,5-triazine intermediate and, thereafter, add component (iii), for example, a hydroxy compound, to produce a 1,3,5-triazine carbamate.

The Organic Solvent (iv)

In the process of the present invention, contacting is carried out in an organic solvent reaction medium. The reaction medium preferably used in the present invention is an organic solvent which is substantially non-reactive with isocyanates i.e., an isocyanate-unreactive organic solvent.

If an hydroxy compound is employed as the isocyanate-reactive component (iii), the reaction medium may comprise a mixture of (a) the organic solvent and (b) hydroxy compound (iii), which, in this instance, may serve as isocyanate-reactive component (i.e. a reactant) and co-solvent. In this mixture, the organic solvent is preferably an isocyanate-unreactive organic solvent. The preferred isocyanate-reactive components which may be used as co-solvent include alcohols having 1 to 20 carbon atoms per molecule, including, for example, alcohols such as methanol, ethanol, propanol, butanol, pentanol, hexanol, heptanol, octanol, nonanol, decanol, lauryl alcohol, 2-ethyl hexanol, alkyl alcohol, glycidol, stearyl alcohol, ethoxyethanol, 1-methoxy-2-propanol, isomers thereof, and mixtures thereof. Solvents having a plurality of functionalities such as ethylene glycol monomethyl ether, methoxypropyl acetate, and the like and mixed solvents are also usable.

Isocyanate-unreactive organic solvents which may be used in the present invention include isocyanate-unreactive polar solvents, isocyanate-unreactive non-polar solvents and mixtures thereof. Isocyanate-unreactive polar solvents are preferred.

Examples of suitable isocyanate-unreactive polar solvents include amides such as N,N-dimethyl acetamide, N-methyl pyrrolidone, N,N-dimethyl formamide, phosphorus-containing compounds such as hexamethyl phosphoramide (HMPA) and hexamethyl phosphorus triamide (HMPT), sulfones such as dimethyl sulfone, sulfolane, sulfoxides such as dimethyl sulfoxide, nitriles such as acetonitrile, propionitrile, benzonitrile, carbonates such as ethylene carbonate, propylene carbonate, butylene carbonate, dimethyl carbonate, lactones such as butyrolactone, propiolactone, nitro compounds such as nitromethane, nitroethane, nitropropane, nitrobenzene, diketones such as acetyl acetone, keto alcohols such as diacetone alcohol, and mixtures thereof. The preferred isocyanate-unreactive polar solvent is N,N-dimethyl acetamide.

Examples of suitable isocyanate-unreactive non-polar solvents include esters such as methyl acetate, ethyl acetate, ethyl formate, methoxypropyl acetate, ketones such as acetone, methyl ethyl ketone, methyl iso-propyl ketone, methyl iso-butyl ketone, cyclohexanone, ethers such as ethylene glycol dimethyl ether, diethylene glycol dimethyl ether, triethylene glycol dimethyl ether, hydrocarbons such as benzene, toluene, ethyl benzene, xylene, mesitylene, hexane, heptane, cyclohexane, halocarbons such as methylene chloride, chlorobenzene, 1,1,1-trichloroethane, and mixtures thereof.

The Novel Process

The novel process of the invention comprises contacting a 1,3,5-triazine derivative of the formula II, above, a cyanate-group-containing reagent, an isocyanate-reactive compound and an organic solvent at a temperature and for a length of time sufficient to produce a 1,3,5-triazine carbamate derivative having at least two carbamate groups. As described above, the organic solvent (i.e., reaction medium) is preferably an isocyanate unreactive organic solvent. Importantly, the isocyanate-unreactive organic solvent employed in the present invention's process must be sufficiently polar to produce an at least bis-carbamate derivative. Preferably, the organic solvent has a dipole moment of at least 3.0 Deby Units. Although a phase transfer catalyst may be used with a sufficiently polar organic solvent to augment the level of substitution and/or reaction rates, it is not required. However, when a non-polar organic solvent is used as the reaction medium, a phase transfer catalyst must be employed. Further, if the organic solvent is polar, however, not sufficiently polar to produce an at least bis-carbamate derivative, a phase transfer catalyst should also be employed to attain the desired bis-carbamate derivative.

Examples of suitable phase transfer catalysts include quaternary salts, crown ethers, and other metal chelating agents. As examples of quaternary salts may be mentioned quaternary ammonium salts, quaternary phosphonium salts and sulfonium salts. Quaternary ammonium salts such as quaternary ammonium halides and cyanates are preferred. Benzyl trialkylammonium chloride, benzyl trialkylammonium bromide, and benzyl trialkylammonium cyanate are especially preferred.

Without being bound by any particular theory, it is believed that the attainment of highly substituted products is dependent on the solubility of the cyanate-group containing reagent (iv) in the reaction medium. That is, for the reaction to proceed at a rate sufficient to produce highly substituted products such as bis- and tris-substituted products, the cyanate group-containing reagent and reaction medium (i.e., organic solvent) should be chosen in such a manner as to result in a sufficient concentration of the cyanate-group containing reagent in the reaction mixture. Thus, when an organic cyanate-group containing reagent such as a quaternary ammonium cyanate is used, solvents of low to moderate polarity can be used in the present process to produce highly substituted products because of the substantial solubility of such reagents in solvents of low polarity. If, on the other hand, an inorganic cyanate group-containing reagent such as sodium or potassium cyanate is used, a solvent of high polarity capable of dissolving such reagents must be used to result in a sufficient concentration of the cyanate-group containing reagent in the reaction mixture, thereby allowing for the production of more highly substituted products (i.e. the bis- and tris-carbamates). Alternatively, if a solvent of low polarity is used with an inorganic-cyanate group containing reagent such as sodium or potassium, a phase transfer catalyst may be needed in the reaction mixture to promote the solubility of the metal cyanate in the low-polar organic solvent, thereby producing sufficient concentrations of an at least bis-carbamate derivative. Whenever a non-polar organic solvent is employed as the reaction medium, a phase transfer catalyst must be present in the reaction mixture, which catalyst, it is believed, serves to promote the solubility of the cyanate-group containing reagent in the non-polar solvent allowing for the production of at least bis-carbamate derivatives.

Contacting may be advantageously carried out in the presence of a catalyst which is substantially non-reactive with component (i), for promoting rapid reaction including, for example, phase transfer catalysts, basic catalysts, and organometallic catalysts.

As examples of basic catalysts may be mentioned strong nitrogenous bases such as amines, imines, amidines and guanidines and inorganic bases such as alkali metal salts. Suitable amines include tertiary amines, including trialkyl amines, triaryl amines, alkyl diaryl amines, dialkyl aryl amines, cyclic amines, bicyclic amines, polycyclic amines, heteroaromatic amines and mixtures thereof, including heteroaromatic amines such as 4-pyrrolidinopyridine, 4-piperidiropyridine, and 4-morpholinopyridine and bicyclic amines such as 1,4-diaza-(2.2.2)-bicyclooctane (DABCO). Of the basic catalysts, 1,4-diaza-(2.2.2)-bicyclooctane (DABCO) and alkylated guanidines such as tetramethylguanidine are preferred.

Suitable examples of organometallic catalysts include organotin compounds such as dibutyltin di-2-ethylhexoate, dibutyltin diisooctyl maleate, dibenzyltin di-2-ethylhexoate, dibutyltin dilaurate, dimethyltin dilaurate (UL-28), tetrabutyl diacetoxy distannoxane (TK-1), tetramethyl diacetoxy distannoxane, tetrapropyl diacetoxy distannoxane, dibutyltin dichloride, and the like.

The molar ratio of cyanate to cyanate-reactive functionality employed in the process of the invention is preferably in the range of from about 10:1 corresponding to a 1000% molar excess quantities to about 1:1 which corresponds to molar equivalent quantities. Preferably, the ratio is in the range of from about 5:1 to about 1:1.

In the process of the present invention, the reaction ingredients are contacted in a suitable reactor at a temperature and length of time sufficient to produce the desired 1,3,5-triazine carbamate. The process may be carried out in any reactor system such as a vessel or container which can be subject to the conditions required to obtain the desired 1,3,5-triazine carbamates.

The reaction components are preferably contacted at a temperature at which the reaction of cyanate groups, on the cyanate-group containing reagent, with the leaving groups on the 1,3,5-triazine derivative proceed at a convenient rate to produce a 1,3,5-triazine carbamate. The reaction of the components is preferably conducted at atmospheric pressure, however, super atmospheric pressures may also be employed, particularly when substantially volatile isocyanate reactive materials are present in the reaction mixture. Preferably, the reaction temperature ranges from about 25° C. to about 160° C., and more preferably from about 80° C. to about 120° C. Under these conditions, the reaction can produce 1,3,5-triazine carbamates within a period of time typically ranging from about 1 hour to about 24 hours.

Since carbamate functional 1,3,5-triazines are the desired product in the present process, the amount of isocyanate reactive compound, i.e., hydroxy compound, will typically be a stoichiometric excess (based upon isocyanate formation). The molar ratio of the isocyanate-reactive functionality added to the isocyanate functionality is generally in the range of from about 10:1 to about 1:1 on the basis of equivalents of isocyanate-reactive functionality per isocyanate group. Preferably, the ratio is in the range of about 3:1 to about 1:1 on such equivalent basis.

The examples which follow are intended as an illustration of certain preferred embodiments of the invention, and no limitation of the invention is implied. NMR spectra were obtained on a Varian Unity 300 Plus. IR spectrum was obtained on a Digilab FTS 60A with 16 scans (Resolution 4). MSEI was conducted on a Kratos MS-50 (Resolution 10K).

EXAMPLE 1

Preparation of tris-(ethoxycarbonylamino)triazine in N,N-Dimethyl Acetamide

Potassium cyanate (15 g) was added, under a nitrogen atmosphere, to a mixture of ethanol (9.6 g) and N,N-dimethyl acetamide (60 ml) in a reactor equipped with an efficient condenser and a stirrer. The reaction mixture was heated to 100° C. and a solution of cyanuric chloride (3.7 g) in N,N-dimethyl acetamide (20 ml) was then added slowly into the reaction mixture over a period of about 10 minutes. The reaction mixture was kept at 100° C. for 6 hours and thereafter at room temperature overnight. The solvent was then removed in vacuo using a rotary evaporator while maintaining the bath temperature at below 80° C. The resulting residue was then added to water (100 ml), the pH adjusted to 7 with concentrated nitric acid, and then extracted with methylene chloride (3×50 ml). The organic layers were combined and dried with anhydrous magnesium sulfate, the solvent was evaporated. Addition of acetonitrile gave crude tris-(ethoxycarbonylamino)triazine as a solid (1.5 g, 22% yield). Recrystallization from ethanol gave pure tris-(ethoxycarbonylamino)triazine as white crystals, m.p. 213–214° C. (uncorrected). It was identified from its infrared spectrum, nuclear magnetic resonance spectra, exact mass in its electron ionization mass spectrum, and by comparison with an authentic sample prepared by known procedures. IR (KBr): 3257, 2983, 1755, 1608, 1492, 1198, 1028, 821 cm$^{-1}$; $^1$H-NMR (300 MHz, DMSO-d$_6$): δ 10.4 (s, NH), 4.2 (q, J=7 Hz, CH$_2$), 1.2 (t, J=7 Hz, CH$_3$); $^{13}$C-NMR (75 MHz, DMSO-d$_6$): δ 163.7, 150.1, 59.6, 13.1; MSEI (M$^+$): m/z found 342.1321; calculated for C$_{12}$H$_{18}$N$_6$O$_6$ 342.1284.

EXAMPLE 2

Preparation of tris-(ethoxycarbonylamino)triazine in N.N-Dimethyl Formamide

The procedure of Example 1 was repeated using N,N-dimethyl formamide as the solvent. Sodium cyanate (5.6 g) was added to a reactor containing ethanol (4.7 g) and N,N-dimethyl formamide (60 ml). A solution of cyanuric chloride (3.7 grams) in N,N-dimethyl formamide (8 ml) was added (10 minutes). After 6 hours at 100° C. and overnight at room temperature, the solution was diluted with methylene chloride (100 ml) and washed twice with water. The organic layer was dried with anhydrous magnesium sulfate. Removal of solvent followed by crystallization using acetonitrile gave tris-(ethoxycarbonylamino)triazine as a white solid (0.4 g, 6% yield). It was identified by $^{13}$C-NMR to be the desired product.

EXAMPLE 3

Preparation of tris-(ethoxycarbonylamino)triazine in Hexamethyl Phosphoramide The procedure of Example 1 was repeated using hexamethyl phosphoramide as the solvent. Potassium cyanate (7.5 g) was added to a reactor containing ethanol (4.7 g) and hexamethyl phosphoramide (40 ml). A solution of cyanuric chloride (3.7 grams) in hexamethyl phosphoramide (10 ml) was added (10 minutes). After 6 hours at 100° C. and overnight at room temperature, the solution was diluted with methylene chloride (100 ml) and washed twice with water. The organic layer was dried with anhydrous magnesium sulfate. Removal of the solvent gave tris-(ethoxycarbonylamino)triazine as a solution in hexamethyl phosphoramide. It was identified by $^{13}$C-NMR to be the desired product.

EXAMPLE 4

Preparation of tris-(ethoxycarbonylamino)triazine in Sulfolane

The procedure of Example 1 was repeated using sulfolane as the solvent. Potassium cyanate (7.5 g) was added to a reactor containing ethanol (4.7 g) and sulfolane (40 ml). A solution of cyanuric chloride (3.7 grams) in sulfolane (10 ml) was added (10 minutes). After 6 hours at 100° C. and overnight at room temperature, the solution was diluted with methylene chloride (100 ml) and washed twice with water. The organic layer was dried with anhydrous magnesium sulfate. Removal of the solvent gave tris-(ethoxycarbonylamino)triazine as a solution in sulfolane. It was identified by $^{13}$C-NMR to be the desired product.

Although the present invention is described with reference to certain preferred embodiments, it is apparent that modifications and variations thereof may be made by those skilled in the art without departing from the scope of this invention as defined by the appended claims.

I claim:

1. A process for preparing a 1,3,5-triazine carbamate derivative having the formula (I):

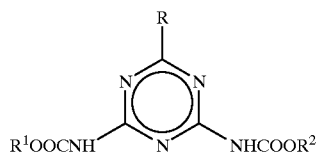

wherein R is selected from the group consisting of—NHCOOR$^3$, hydrogen, hydrocarbyl, hydrocarbyloxy, hydrocarbylthio, amido, sulfonamido, and a leaving group; and wherein R$^1$, R$^2$ or R$^3$ is, independently, a hydrocarbyl or a hydrocarbyloxyhydrocarbyl, said process comprising the steps of contacting:

(i) a 1,3,5-triazine derivative having at least two cyanate-displaceable leaving groups, represented by the formula (II):

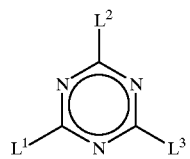

wherein L$^1$ is selected from the group consisting of hydrogen, hydrocarbyl, hydrocarbyloxy, hydrocarbylthio, amido, sulfonamido, amino and a leaving group; and wherein each of L$^2$ and L$^3$ is, independently, a leaving group;

wherein said leaving group is selected from the group consisting of halogen, a tertiary amino group and a sulfonate group;

(ii) a cyanate-group containing reagent capable of reaction therewith;

(iii) an isocyanate-reactive compound; and (iv) an isocyanate-unreactive organic solvent, wherein said contacting is carried out at a temperature and length of time sufficient to produce a 1,3,5-triazine carbamate derivative having at least two carbamate groups, with the proviso that if the organic solvent is not sufficiently polar to produce a bis-carbamate derivative, contacting is carried out in the presence of a phase-transfer catalyst.

2. The process of claim 1, wherein the isocyanate-unreactive organic solvent is a polar solvent having a dipole moment of at least 3.0 Deby Units.

3. The process of claim 1, wherein the isocyanate-unreactive organic solvent has a dipole moment of less than 3.0 Deby Units and contacting is carried out in the presence of a phase transfer catalyst.

4. The process of claim 1, wherein R is —NHCOOR³ and R¹, R² and R³ are hydrocarbyl compounds.

5. The process of claim 4, wherein the hydrocarbyl compound is an alkyl group having from 1 to 8 carbon atoms.

6. The process of claim 5, wherein $R^1$, $R^2$ and $R^3$ is, independently, methyl or normal butyl.

7. The process of claim 1, wherein each of $L^1$, $L^2$ and $L^3$ is, independently, a halogen.

8. The process of claim 7, wherein the halogen is a chloride.

9. The process of claim 1 wherein cyanate-group containing reagent (ii) is represented by the formula:

$$W(NCO)_n$$

wherein n is at least 1; and
wherein W is selected from the group consisting of metal, hydrogen, quaternary ammonium, quaternary phosphonium, sulfonium, silyl and mixtures thereof.

10. The process of claim 9, wherein W is selected from the group consisting of sodium, potassium, tetraalkylammonium, aryltrialkylammonium, and a mixture thereof.

11. The process of claim 1, wherein the isocyanate-reactive compound (iii) is a hydroxy-functional compound.

12. The process of claim 11, wherein the hydroxy-functional compound is an alcohol having from 1 to 20 carbon atoms.

13. The process of claim 12, wherein the alcohol is selected from the group consisting of methanol, ethanol, propanol, butanol, pentanol, hexanol, heptanol, octanol, nonanol, decanol, lauryl alcohol, 2-ethyl hexanol, alkyl alcohol, glycidol, stearyl alcohol, 1-methoxy-2-ethanol, 1-ethoxy-2-ethanol, 1-methoxy-2-propanol, 1-ethoxy-2-propanol, isomers thereof, and mixtures thereof.

14. The process of claim 13, wherein the alcohol is selected from the group consisting of methanol, butanol and mixtures thereof.

15. The process of claim 1, wherein the isocyanate-unreactive organic solvent is selected from the group consisting of an amide, a phosphorus-containing compound, a sulfone, a sulfoxide, a nitrile, a carbonate, a lactone, a nitro compound, a diketone, a keto alcohol, a ketone, an ether, an ester, a hydrocarbon, a halocarbon, and a mixture thereof.

16. The process of claim 15 wherein the isocyanate-unreactive solvent is selected from the group consisting of N,N-dimethyl acetamide, N-methyl pyrrolidone, N,N-dimethyl formamide, hexamethyl phosphoramide (HMPA), hexamethyl phosphorus triamide (HMPT), dimethyl sulfone, sulfolane, acetonitrile, propionitrile, benzonitrile, ethylene carbonate, propylene carbonate, butylene carbonate, dimethyl carbonate, butyrolactone, propiolactone, nitromethane, nitroethane, nitropropane, nitrobenzene, acetyl acetone, diacetone alcohol, methyl acetate, ethyl acetate, ethyl formate, methoxypropyl acetate, acetone, methyl ethyl ketone, methyl iso-propyl ketone, methyl iso-butyl ketone, cyclohexanone, ethylene glycol dimethyl ether, diethylene glycol dimethyl ether, triethylene glycol dimethyl ether, benzene, toluene, ethyl benzene, xylene, mesitylene, hexane, heptane, cyclohexane, methylene chloride, chlorobenzene, 1,1,1-trichloroethane, and a mixtures thereof.

17. The process of claim 16 wherein the isocyanate-unreactive organic solvent is a polar solvent selected from the group consisting of N,N-dimethyl acetamide, N-methyl pyrrolidone, N,N-dimethyl formamide, hexamethyl phosphoramide (HMPA), hexamethyl phosphorus triamide (HMPT), dimethyl sulfone, sulfolane, dimethyl sulfoxide, acetonitrile, propionitrile, benzonitrile, ethylene carbonate, propylene carbonate, butylene carbonate, dimethyl carbonate, butyrolactone, propiolactone, nitromethane, nitroethane, nitropropane, nitrobenzene, acetyl acetone, diacetone alcohol, and mixtures thereof.

18. The process of claim 16, wherein the isocyanate-unreactive solvent is a non-polar solvent selected from the group consisting of methyl acetate, ethyl acetate, ethyl formate, methoxypropyl acetate, acetone, methyl ethyl ketone, methyl iso-propyl ketone, methyl iso-butyl ketone, cyclohexanone, ethylene glycol dimethyl ether, diethylene glycol dimethyl ether, triethylene glycol dimethyl ether, benzene, toluene, ethyl benzene, xylene, mesitylene, hexane, heptane, cyclohexane, methylene chloride, chlorobenzene, 1,1,1-trichloroethane, and mixtures thereof.

19. The process of claim 1, wherein ingredients (i), (ii), and (iv) are first contacted, and thereafter, ingredient (iii) is contacted.

20. The process of claim 1, wherein ingredients (i), (ii), (iii), and (iv) are simultaneously contacted.

21. The process of claim 1, wherein the phase transfer catalyst is selected from the group consisting of quaternary salts and crown ethers.

22. A process for preparing a 1,3,5-triazine carbamate derivative having the formula (I):

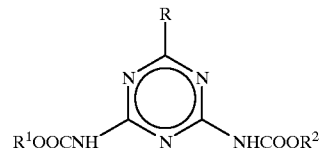

wherein R is selected from the group consisting of —NHCOOR³, hydrogen, hydrocarbyl, hydrocarbyloxy, hydrocarbylthio, amido, sulfonamido, and a leaving group; and
wherein $R^1$, $R^2$ or $R^3$ is, independently, a hydrocarbyl or a hydrocarbyloxyhydrocarbyl,
said process comprising the steps of contacting:
(i) a 1,3,5-triazine derivative having at least two cyanate-displaceable leaving groups, represented by the formula (II):

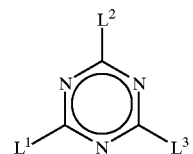

wherein $L^1$ is selected from the group consisting of hydrogen, hydrocarbyl, hydrocarbyloxy, hydrocarbylthio, amido, sulfonamido, amino and a leaving group; and
wherein each of $L^2$ and $L^3$ is, independently, a leaving group;
wherein said leaving group is selected from the group consisting of halogen, a tertiary amino group and a sulfonate group;
(ii) a cyanate-group containing reagent capable of reaction therewith;
(iii) a hydroxy-functional compound; and
(iv) an isocyanate-unreactive polar organic solvent, wherein said contacting is carried out at a temperature and length of time sufficient to produce a 1,3,5-triazine carbamate derivative having at least two carbamate groups.

23. The process of claim 22, wherein the isocyanate-unreactive polar organic solvent has a dipole moment of at least 3.0 Deby Units.

24. The process of claim 22, wherein the isocyanate-unreactive polar organic solvent has a dipole moment of less than 3.0 Deby Units.

25. The process of claim 24, wherein the reaction mixture further comprises a phase transfer catalyst.

26. The process of claim 25, wherein the phase transfer catalyst is selected from the group consisting of quaternary salts and crown ethers.

27. The process of claim 22 wherein the isocyanate-unreactive polar organic solvent is selected from the group consisting of an amide, a phosphorus-containing compound, a sulfone, a sulfoxide, a carbonate, a lactone, a nitro compound, a diketone, a keto alcohol, and mixtures thereof.

28. The process of claim 27 wherein the isocyanate-unreactive polar solvent is selected from the group consisting of N,N-dimethyl acetamide, N-methyl pyrrolidone, N,N-dimethyl formamide, hexamethyl phosphoramide (HMPA), hexamethyl phosphorus triamide (HMPT), dimethyl sulfone, sulfolane, nitriles such as acetonitrile, propionitrile, benzonitrile, carbonates such as ethylene carbonate, propylene carbonate, butylene carbonate, dimethyl carbonate, butyrolactone, propiolactone, nitromethane, nitroethane, nitropropane, acetyl acetone, diacetone alcohol, and a mixture thereof.

29. The process of claim 28 wherein the isocyanate-unreactive polar solvent is selected from the group consisting of N,N-dimethyl acetamide, N-methyl pyrrolidone, N,N-dimethyl formamide, hexamethyl phosphoramide (HMPA), hexamethyl phosphorus triamide (HMPT), dimethyl sulfone, sulfolane, and mixtures thereof.

30. A process for preparing a 1,3,5-triazine carbamate derivative having the formula (I):

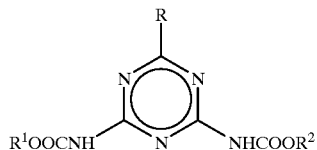

wherein R is selected from the group consisting of —NHCOOR³, hydrogen, hydrocarbyl, hydrocarbyloxy, hydrocarbylthio, amido, sulfonamido, and leaving group; and
wherein R¹, R² or R³ is, independently, a hydrocarbyl or a hydrocarbyloxyhydrocarbyl,
said process comprising the steps of contacting:
(i) a 1,3,5-triazine derivative having at least two cyanate-displaceable leaving groups, represented by the formula (II):

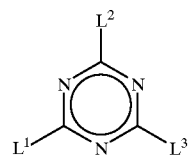

wherein L¹ is selected from the group consisting of hydrogen, hydrocarbyl, hydrocarbyloxy, hydrocarbylthio, amido, sulfonamido, amino and a leaving group; and
wherein each of L² and L³ is, independently, a leaving group;
wherein said leaving group is selected from the group consisting of halogen, a tertiary amino group and a sulfonate group;
(ii) a cyanate-group containing reagent capable of reaction therewith;
(iii) a hydroxy-functional compound;
(iv) an isocyanate-unreactive non-polar organic solvent; and
(v) a phase-transfer catalyst;
wherein said contacting is carried out at a temperature and length of time sufficient to produce a 1,3,5-triazine carbamate derivative having at least two carbamate groups.

31. The process of claim 30 wherein the isocyanate-unreactive non-polar solvent is selected from the group consisting of an ester, ether, a ketone, a hydrocarbon, a halocarbon, and mixtures thereof.

32. The process of claim 31 wherein the isocyanate-unreactive non-polar solvent is selected from the group consisting of methyl acetate, ethyl acetate, ethyl formate, methoxypropyl acetate, acetone, methyl ethyl ketone, methyl iso-propyl ketone, methyl iso-butyl ketone, cyclohexanone, ethylene glycol dimethyl ether, diethylene glycol dimethyl ether, triethylene glycol dimethyl ether, benzene, toluene, ethyl benzene, xylene, mesitylene, hexane, heptane, cyclohexane, methylene chloride, chlorobenzene, 1,1,1-trichloroethane, and mixtures thereof.

33. A process for preparing a 1,3,5-triazine carbamate derivative having at least two carbamate groups, represented by the formula (I):

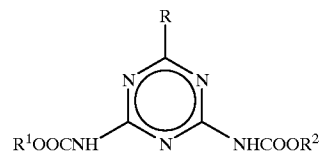

wherein R is selected from the group consisting of —NHCOOR³, hydrogen, hydrocarbyl, hydrocarbyloxy, hydrocarbylthio, amido, sulfonamido, and a leaving group; and
wherein R¹, R² or R³ is, independently, a hydrocarbyl or a hydrocarbyloxyhydrocarbyl,
said process comprising the steps of contacting:
(i) a 1,3,5-triazine derivative having at least two cyanate-displaceable leaving groups, represented by the formula (II):

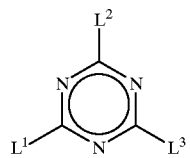

wherein L¹ is selected from the group consisting of hydrogen, hydrocarbyl, hydrocarbyloxy, hydrocarbylthio, amido, sulfonamido, amino and a leaving group; and
wherein each of L² and L³ is, independently, a leaving group;

wherein said leaving group is selected from the group consisting of halogen, a tertiary amino group and a sulfonate group;

(ii) a cyanate-group containing reagent capable of reaction therewith;

(iii) a hydroxy-functional compound; and (iv) an isocyanate-unreactive organic solvent, wherein said contacting is carried out at a temperature in the range of from about 25° C. to about 160° C. and length of time in the range of from about 1 hour to about 24 hours, with the proviso that if the organic solvent has a dipole moment of less than 3.0 Deby Units, contacting is carried out in the presence of a phase-transfer catalyst.

* * * * *